United States Patent [19]

Akins

[11] Patent Number: Plant 5,838

[45] Date of Patent: Dec. 23, 1986

[54] APPLE TREE 'LORIGLO'

[76] Inventor: Amol O. Akins, Rte. 1, Whitesville, Ky. 42378

[21] Appl. No.: 495,097

[22] Filed: Aug. 3, 1983

[51] Int. Cl.[4] ..... A01H 5/00

[52] U.S. Cl. ..... Plt./34

[58] Field of Search ..... Plt./34

[56] References Cited

U.S. PATENT DOCUMENTS

P.P. 85 1/1934 Uecker ..... Plt./34

P.P. 2,650 7/1966 Snyder ..... Plt./34

P.P. 2,934 10/1969 Robison et al. ..... Plt./34

P.P. 5,086 8/1983 Carnefix ..... Plt./34

*Primary Examiner*—James R. Feyrer

*Attorney, Agent, or Firm*—Bailey & Hardaway

[57] ABSTRACT

A new and distinct variety of apple tree known as Loriglo as shown and described being characterized particularly as to novelty by fruit maturing about two weeks before the Red Delicious with a very attractive appearance not quite so intensely red as the Red Delicious.

1 Drawing Figure

The The present invention relates to a new and distinct variety of apple tree discovered as a limb sport of a Jonathan apple tree.

The new sport was asexually reproduced by topworking by grafting the new variety. When the topworked trees came into bearing, it was positively observed that the fruit unmistakably resembled the fruit of the original sport. The fruit matures about two weeks before the Red Delicious, and when mature, it has a very attractive appearance and spicy delicious flavor with color not quite so intense as the Red Delicious.

The tree was found as a bud sport on a Jonathan Tree growing in a cultivated orchard with mostly Red Delicious Trees. The limb sport differed from the remainder of the tree by a slight difference in color of the leaves and a difference in the color and flavor of the fruit in that it was generally bright red in comparision to a darker duller color of the Jonathan and more delicious than the fruit of the parent tree. The bearing habit of the tree is regular and the growth habit is not spur type and the pollination is self-pollinating. The blossoms are larger and white compared to a smaller pink blossom of the Jonathan. The Loriglo apple of the present tree is more conical than the Jonathan which is a flat apple.

Loriglo has a much better flavor than Jonared. The color pattern is different and more attractive in that it is a brighter red and the blush fades into the ground color making it an attractive yellow with hints of pink. The Loriglo does not resemble Jonared, Blackjon and Jonnee having different color patterns and flavor. Blackjon and Jonnee resemble Jonared but not Loriglo.

THE TREE

The tree was grown and observed at Whitesville, Ky. The date of the first picking was August 25th and the last picking was September 8th, ripening about two weeks earlier than the Red Delicious.

Tree: Medium size; vigorous; productive; spreading; globular in shapes; regular bearer.

*Trunk.*—Medium and smooth, light brown.

*Branches.*—Medium smooth and moderate branching. Color 10RP5/2; lenticels gray numerous and elongated.

*Leaves.*—Medium to large; medium width; medium length, oval, tip-pointed; medium serration; Petiole medium. Length — 4 inches. Width — 2¾ inches. Leaf color, underside R.H.S. Yellow — Green group 148 C, topside Green Group 137 A.

Flowers:

*Dates of first and full bloom.*—April 28th to May 5th, respectively; slightly earlier than Red Delicious.

*Color.*—Light pink petals with darker pink calyx.

Fruit:

*Maturity when described.*—Firm ripe.

*Size.*—Uniform. Axial diameter — 2½ inches. Transverse diameter — 3 inches.

*Form.*—Round, oblong. The fruit is round when viewed from above.

*Stem cavity.*—Symmetrical. Depth — ⅝th inches. Breadth — 1 inch. Markings: color-greenish yellow.

*Basin.*—Symmetrical; rounded; smooth, basin open sepals; pubescent and yellowish green. Depth — ½ inch.

*Stem.*—¾ inch, medium, larger at tip.

*Skin.*—Medium thickness, tough and smooth. Lenticels numerous slightly raised dots, oblong and yellowish, more numerous towards blossom end. Ground color-pink. Markings — striped; bright red color.

*Bloom.*—None.

*Color.*—Apple color R.H.S., Red Group 42 B, with some areas nearing gray, Red Group 179 B.

*Flesh.*—Medium juicy. Color-white with yellowish tinge. Texture — firm; crisp. Flavor — slightly acid. Aroma — very little. Quality — good.

*Cuticle.*—Near Yellow-Green Group 145 C, normal foliage russeting near stem attachment, fruit oxidizes rapidly, fruit color Yellow-White Group 158 A oxidizes to a near Yellow-White Group 158 A. Russeting color Gray-Orange Group 164 B.

*Core.*—Bundle area-medium; cordate; symmetrical at base. Halves of core equal. Bundles — conspicuous. Core lines-clasping. Carpellary area — distinct; medium. Calyx tube-pubescent toward base, funnel form, long; depth of tube to shoulder — ⅓ inch; entire depth — ⅔ inch. Styles — present. Stamens — in whorl. Seed cells — open; cell walls — medium; Seed cells — axil, small and open; cell walls — thin, tough, length about — $\frac{3}{4}$ inch; breadth — about $\frac{1}{4}$ inch; longitudinal section — obovate; cross section — narrow; surface tufted.

*Seeds.*—Average number. Ten — most cells having 2 seeds. Breadth — about $\frac{1}{8}$ inch. Color — Dark brown.

Use: Market; dessert.

Keeping quality: Good; about 100 days in ordinary storage.

References: *Munsell Book of Color* and R.H.S. Colour Chart.

BRIEF DESCRIPTION OF THE DRAWING

The accompanying drawing shows whole apples of the variety in side and stem and views; the top and bottom sides of typical leaves; as well as a third apple split on its vertical axis. Color specifications are from *Munsell Book of Color* and R.H.S. Colour Chart.

What is claimed is:

1. A new and distinct variety of apple tree, substantially as shown and described, characterized particularly as to novelty by a unique combination of characteristics, including fruit maturing about two weeks before the Red Delicious with a very attractive appearance and spicy delicious flavor with an attractive red color which is not quite so intense as the Red Delicious.

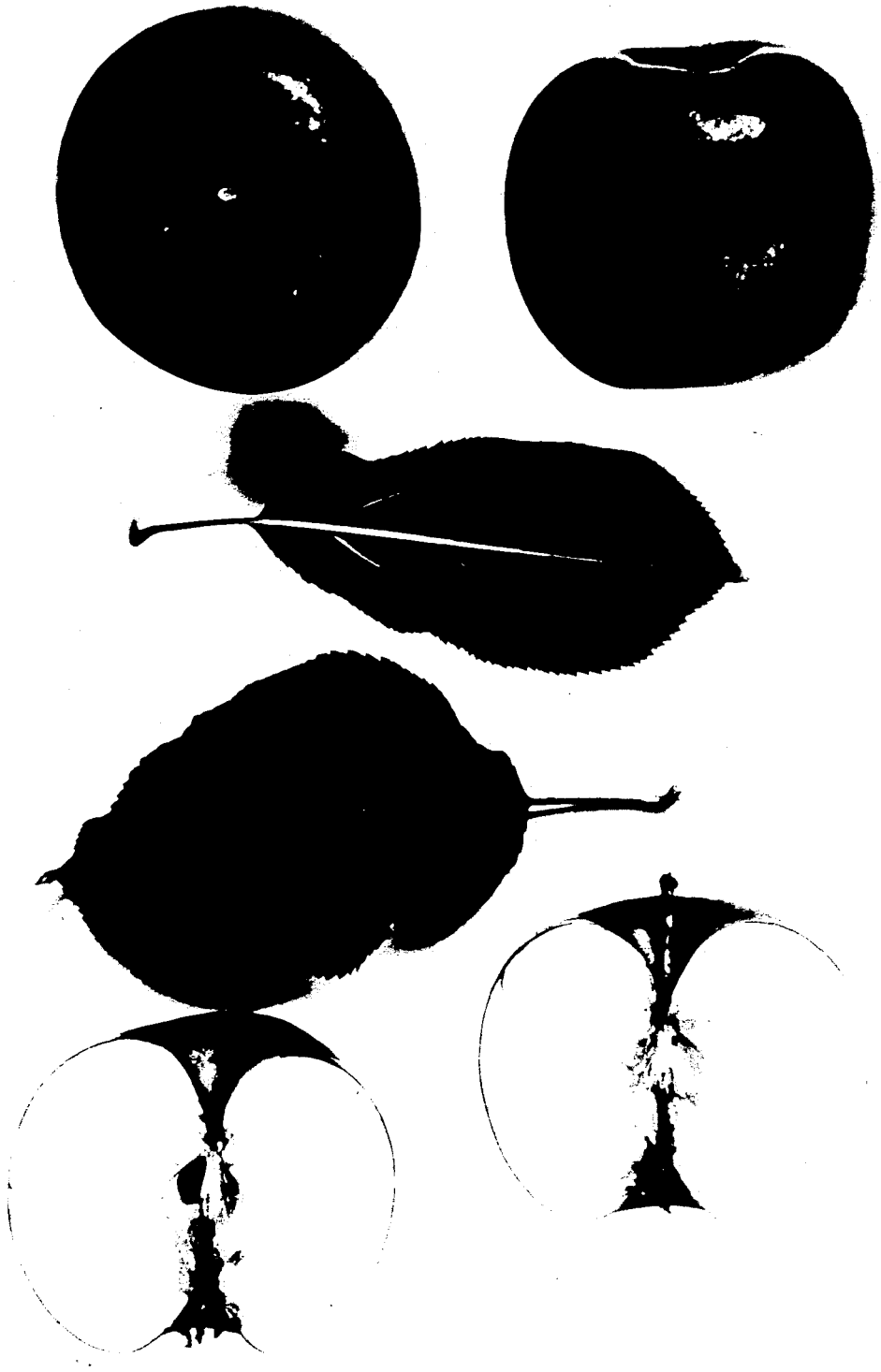

* * * * *